(12) United States Patent
Dhanvijay

(10) Patent No.: US 10,723,804 B2
(45) Date of Patent: Jul. 28, 2020

(54) MONOCLONAL ANTIBODIES

(71) Applicant: Cytosystems Limited, Aberdeen (GB)

(72) Inventor: Sushant Dhanvijay, Aberdeen (GB)

(*) Notice: Subject to any disclaimer, the term of this patent is extended or adjusted under 35 U.S.C. 154(b) by 72 days.

(21) Appl. No.: 15/739,420

(22) PCT Filed: Jun. 23, 2016

(86) PCT No.: PCT/GB2016/051873
§ 371 (c)(1),
(2) Date: Dec. 22, 2017

(87) PCT Pub. No.: WO2016/207632
PCT Pub. Date: Dec. 29, 2016

(65) Prior Publication Data
US 2018/0171022 A1    Jun. 21, 2018

(30) Foreign Application Priority Data
Jun. 25, 2015  (GB) .................................. 1511196.6

(51) Int. Cl.
| | | |
|---|---|---|
| *C07K 16/30* | (2006.01) | |
| *C07K 16/18* | (2006.01) | |
| *C07K 19/00* | (2006.01) | |
| *G01N 33/574* | (2006.01) | |

(52) U.S. Cl.
CPC .............. *C07K 16/30* (2013.01); *C07K 16/18* (2013.01); *C07K 16/3038* (2013.01); *C07K 19/00* (2013.01); *G01N 33/574* (2013.01); *C07K 2317/24* (2013.01); *C07K 2317/92* (2013.01); *G01N 2800/60* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 6,303,323 B1 | 10/2001 | Laskey | |
| 7,056,690 B2* | 6/2006 | Laskey | G01N 33/57484 435/7.23 |
| 2005/0250166 A1 | 11/2005 | Masai | |
| 2014/0357512 A1 | 12/2014 | Yang | |

FOREIGN PATENT DOCUMENTS

| | | |
|---|---|---|
| EP | 0120694 | 4/1984 |
| EP | 0125023 | 11/1984 |
| EP | 2605017 | 6/2013 |
| JP | 2012254084 | 2/2014 |
| WO | WO99/21014 | 4/1999 |
| WO | WO2005/095964 | 10/2005 |
| WO | WO2006/116442 | 11/2006 |
| WO | WO2009/156711 | 12/2009 |
| WO | WO2012/093251 | 7/2012 |

OTHER PUBLICATIONS

King et al (Cancer Research, 66:219, Apr. 1, 2006, cited in IDS).*
GenBank Accession No. X67334 (printed Jul. 2019).*
King et al (2006) Cancer Res 66: 219, Apr. 1, 2006.
Uniprot D3ZP96 Apr. 20, 2010.
Uniprot Q3UJN1 Oct. 11, 2005.
Dudderidge et al Clin Cancer Res 11: 2510; Apr. 1, 2005.
Obermann et al BMC Cancer 5: 162, Dec. 20, 2005.
Meng et al Clin Cancer Red 7:271, 2Sep. 1, 2001.

* cited by examiner

*Primary Examiner* — Laura B Goddard
(74) *Attorney, Agent, or Firm* — QIPLG; Gary Baker

(57) ABSTRACT

The invention relates to an isolated antigenic polypeptide comprising an epitope for binding an MCM2 monoclonal antibody, wherein the polypeptide comprises an amino acid sequence selected from the group consisting of: (a) the amino acid as shown in FIG. 1; and (b) the amino acid sequence wherein said sequence is a variant polypeptide modified by addition, deletion or substitution of at least one amino acid residue as represented in FIG. 1.

7 Claims, 5 Drawing Sheets

Figure 6:
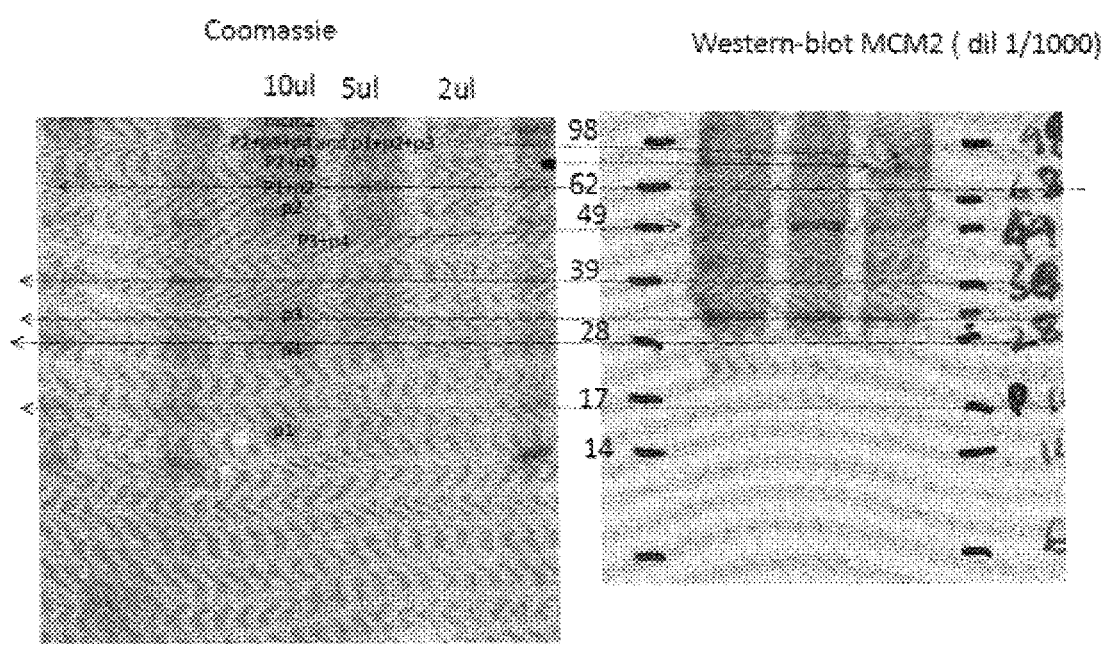

Specification includes a Sequence Listing.

SHVRHH

FIG. 1

VGSHVRHHP

FIG. 2

1 maessesftm asspaqrrrg ndpltsspgr ssrrtdalts spgrdlppfe deseglIgte
   61 gpleeeedge eligdgmerd yraipelday eaeglaldde dveeltasqr eaaeramrqr
  121 dreagrglgr mrrgllydsd eedeerpark rrqverated geedeemies ienledlkgh
  181 svrewvsmag prleihhrfk nflrthvdsh ghnvfkeris dmckenresl vvnyedlaar
  241 ehvlayflpe apaellqifd eaalevvlam ypkydritnh ihvrishlpl veelrslrql
  301 hlnqlirtsg vvtsctgvlp qlsmvkyncn kcnfvlgpfc qsqnqevkpg scpecqsagp
  361 fevnmeetiy qnyqririqe spgkvaagrl prskdailla dlvdsckpgd eieltgiyhn
  421 nydgslntan gfpvfatvil anhvakkdnk vavgeltded vkmitslskd qqigekifas
  481 iapsiyghed ikrglalalf ggepknpggk hkvrgdinvl lcgdpgtaks qflkyiekvs
  541 sraifttgqg asavgltayv qrhpvsrewt leagalvlad rgvclidefd kmndqdrtsi
  601 heameqqsis iskagivtsl qarctviaaa npiggrydps ltfsenvdlt epiisrfdil
  661 cvvrdtvdpv qdemlarfvv gshvrhhpsn keeeglangs aaepampnty gveplpqevl
  721 kkyiiyaker vhpklnqmndq dkvakmysdl rkesmatgsi pitvrhiesm irmaeahari
  781 hlrdyviedd vnmairvmle sfidtqkfsv mrsmrktfar ylsfrrdnne lllfilkqlv
  841 aeqvtyqmr fgaqqdtiev pekdlvdkar qinihnlsaf ydselfrmnk fshdlkrkmi
  901 lqqf

FIG. 3 ggatccgcatccagcccggcccagcgtcggcgaggcaatgatcctctcacctccagccctggccgaagctcccggcgta
ctgatgccctcacctccagccctggccgtgaccttccaccatttgaggatgagtccgaggggctcctaggcacagagggg
cccctggaggaagaagaggatggagaggagctcattggagatggcatggaaagggactaccgcgccatcccagagctg
gacgcctatgaggccgagggactggctctggatgatgaggacgtagaggagctgacggccagtcagagggaggcagc
agagcgggccatgcggcagcgtgaccggaggctggccggggcctgggccgcatgcgccgtgggctcctgtatgaca
gcgatgaggaggacgaggagcgccctgcccgcaagcgccgccaggtggagcgggccacggaggacggcgtggag
gacgaggagatgatcgagtgcatcgagtacctggaggatctcaatggccactctgtgcgcgagtgggtgagcatggcg
ggccccggctggagatccaccaccgcttcaagaacttcctgcgcactcacgtcgacagccacggccacaacgtcttcaa
ggagcgcatcagcgacatgtgcaaagagaaccgtgagagcctggtggtgaactatgaggacttggcagccagggagca
cgtgctggcctacttcctgcctgaggcaccggcggagctgctgcagatctttgatgaggctgccctggaggtggtactggc
catgtaccccaagtacgaccgcatcaccaaccacatccatgtccgcatctcccacctgcctctggtggaggagctgcgctc
gctgaggcagctgcatctgaaccagctgatccgcaccagtggggtggtgaccagctgcactggcgtcctgccccagctca
gcatggtcaagtacaactgcaacaagtgcaattcgtcctgggtcctttctgccagtcccagaaccaggaggtgaaaccag
gctcctgcctgagtgccagtcggccggcccctttgaggtcaacatggaggagaccatctatcagaactaccagcgtatcc
gaatccaggagagtccaggcaaagtggcggctggccggctgccccgctccaaggacgccattctcctcgcagatctggt
ggacagctgcaagccaggagacgagatagagctgactggcatctatcacaacaactatgatggctcccicaacactgcca
atggcttccctgtctttgccactgtcatcctagccaaccacgtggccaagaaggacaacaaggttgctgtaggggaactgac
cgatgaagatgtgaagatgatcactagcctctccaaggatcagcagatcggagagaagatctttgccagcattgctccttcc
atctatggtcatgaagacatcaagagaggcctggctctggccctgttcggaggggagcccaaaaacccaggtggcaagc
acaaggtacgtggtgatatcaacgtgctcttgtgcggagacccttggcacagcgaagtcgcagtttctcaagtatattgagaa
agtgtccagccgagccatcttcaccactggccagggggcgtcggctgtggcctcacggcgtatgtccagcggcaccct
gtcagcaggagtggaccttggaggctggggccctggttctggctgaccgaggagtgtgtctcattgatgaatttgacaag
atgaatgaccaggacagaaccagcatccatgaggccatggagcaacagagcatctccatctcgaaggctggcatcgtca
cctccctgcaggctcgctgcacggtcattgctgccgccaacccatagggaggggcgctacgacccctcgctgactttctctg
agaacgtggacctcacagagcccatcatctcacgctttgacatcctgtgtgtggtgagggacaccgtggacccagtccagg
acgagatgctggcccgcttcgtggtgggcagccacgtcagacaccaccccagcaacaaggaggaggagggggctggcc
aatggcagcgctgctgagcccgccatgcccaacacgtatggcgtggagcccctgccccaggaggtcctgaagaagtaca
tcatctacgccaaggagagggtccacccgaagctcaaccagatggaccaggacaaggtggccaagatgtacagtgacct
gaggaaagaatctatggcgacaggcagcatcccattacggtgcggcacatcgagtccatgatccgcatggcggaggcc
cacgcgcgcatccatctgcgggactatgtgatcgaagacgacgtcaacatggccatccgcgtgatgctggagagcttcata
gacacacagaagttcagcgtcatgcgcagcatgcgcaagactttgcccgctacctttcattccggcgtgacaacaatgag
ctgttgctcttcatactgaagcagttagtggcagagcaggtgacatatcagcgcaaccgctttggggcccagcaggacact
attgaggtccctgagaaggacttggtggataaggctcgtcagatcaacatccacaacctctctgcatttatgacagtgagct
cttcaggatgaacaagttcagccacgacctgaaaaggaaaatgatcctgcagcagttctgagaattc

FIG. 4

MSPILGYWKIKGLVQPTRLLLEYLEEKYEEHLYERDEGDKWRNKKFELGLEF
PNLPYYIDGDVKLTQSMAIIRYIADKHNMLGGCPKERAEISMLEGAVLDIRYG
VSRIAYSKDFETLKVDFLSKLPEMLKMFEDRLCHKTYLNGDHVTHPDFMLYD
ALDVVLYMDPMCLDAFPKLVCFKKRIEAIPQIDKYLKSSKYIAWPLQGWQAT
FGGGDHPPKSDLEVLFQGPLGSASSPAQRRGNDPLTSSPGRSSRRTDALTSSP
GRDLPPFEDESEGLLGTEGPLEEEEDGEELIGDGMERDYRAIPELDAYEAEGL
ALDDEDVEELTASQREAAERAMRQRDREAGRGLGRMRRGLLYDSDEEDEER
PARKRRQVERATEDGEEDEEMIESIENLEDLKGHSVREWVSMAGPRLEIHHRF
KNFLRTHVDSHGHNVFKERISDMCKENRESLVVNYEDLAAREHVLAYFLPEA
PAELLQIFDEAALEVVLAMYPKYDRITNHIHVRISHLPLVEELRSLRQLHLNQL
IRTSGVVTSCTGVLPQLSMVKYNCNKCNFVLGPFCQSQNQEVKPGSCPECQS
AGPFEVNMEETIYQNYQRIRIQESPGKVAAGRLPRSKDAILLADLVDSCKPGD
EIELTGIYHNNYDGSLNTANGFPVFATVILANHVAKKDNKVAVGELTDEDVK
MITSLSKDQQIGEKIFASIAPSIYGHEDIKRGLALALFGGEPKNPGGKHKVRGD
INVLLCGDPGTAKSQFLKYIEKVSSRAIFTTGQGASAVGLTAYVQRHPVSREW
TLEAGALVLADRGVCLIDEFDKMNDQDRTSIHEAMEQQSISISKAGIVTSLQA
RCTVIAAANPIGGRYDPSLTFSENVDLTEPIISRFDILCVVRDTVDPVQDEMLA
RFVVGSHVRHHPSNKEEEGLANGSAAEPAMPNTYGVEPLPQEVLKKYIIYAK
ERVHPKLNQMDQDKVAKMYSDLRKESMATGSIPITVRHIESMIRMAEAHARI
HLRDYVIEDDVNMAIRVMLESFIDTQKFSVMRSMRKTFARYLSFRRDNNELL
LFILKQLVAEQVTYQRNRFGAQQDTIEVPEKDLVDKARQINIHNLSAFYDSEL
FRMNKFSHDLKRKMILQQF*

FIG. 5

MCM2 antibody Batch 1

MCM2 Antibody batch 2

MONOCLONAL ANTIBODIES

FILED OF THE INVENTION

The invention relates to antibodies capable of binding to MCM2 and methods of using these antibodies, particularly in the diagnosis of cancer.

BACKGROUND TO THE INVENTION

Cancer is an abnormal disease state in which uncontrolled proliferation of one or more cell populations interferes with normal biological function. The proliferative changes are usually accompanied by other changes in cellular properties, including reversion to a less organised state. Cancer cells are typically referred to as "transformed". Transformed cells generally display several of the following properties: spherical morphology, expression of foetal antigens, growth-factor independence, lack of contact inhibition, anchorage-independence, and growth to high density. Cancer cells form tumours and are referred to as "primary" or "secondary" tumours. A primary tumour results in cancer cell growth in an organ in which the original transformed cell develops. A secondary tumour results from the escape of a cancer cell from a primary tumour and the establishment of a secondary tumour in another organ. The process is referred to as metastasis and this process may be aggressive, for example as in the case of hepatoma or lung cancer.

Previous studies have identified minichromosome maintenance proteins (MCM) as key regulators in the cell cycling process of epithelial tissue (see WO99/21014 and Gonzalez et al; Nature Reviews/Cancer, Vol 5: pp 135-141, February 2005). MCMs were identified as useful biomarkers of "cell cycle state", i.e. whether a cell is capable of proliferating rather than being quiescent or senescent. Expression of all 6 MCMs (MCM2-7) is seen throughout all phases of the cell cycle and is down regulated following exit from the cell cycle into quiescence, differentiation or senescence. A monoclonal antibody to an MCM such as MCM2 is known to have utility in the diagnosis of some cancers such as cervical cancer (WO2006/116442) prostate (WO2009/156711) and bladder (WO2012/093251) cancer.

Accordingly, there is a need for a novel and effective monoclonal antibodies capable of specifically binding to MCM2.

STATEMENTS OF THE INVENTION

The present inventors have now developed novel monoclonal antibodies which have substantially improved binding affinities for MCM2 and are highly effective as a diagnostic tool for cancer in particular prostate and bladder cancers.

According to a first aspect of the invention there is provided an isolated antigenic polypeptide comprising an epitope for binding an MCM2 monoclonal antibody, wherein the polypeptide comprises an amino acid sequence selected from the group consisting of:
 (a) the amino acid as shown in FIG. 1; and
 (b) the amino acid sequence wherein said sequence is a variant polypeptide modified by addition, deletion or substitution of at least one amino acid residue as represented in FIG. 1.

As used herein, "epitope" is intended the part of an antigenic molecule to which an antibody is produced and to which the antibody will bind. An "MCM2 epitope" comprises the part of the MCM2 protein to which an MCM2 monoclonal antibody binds.

A modified polypeptide or variant polypeptide may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In one embodiment, the variant polypeptides have at least 85% identity, more preferably at least 90% identity, even more preferably at least 95% identity, still more preferably at least 97% identity, and most preferably at least 99% identity with the full length amino acid sequences illustrated herein. Thus the polypeptide of the invention has at least 90% sequence identity to the amino acid as shown in FIG. 1 or FIG. 2 wherein the polypeptide has antigenic activity.

In a preferred embodiment of the invention said polypeptide is represented by the amino acid sequence in FIG. 2, or antigenic part thereof.

As used herein "part of" may include a polypeptide fragment which may be at least 10 amino acids long, for example at least 8, 7, 6, 5 or 4 amino acids long.

As used herein, the term "polypeptide" means, in general terms, a plurality of amino acid residues joined together by peptide bonds. It is used interchangeably and means the same as peptide, protein, oligopeptide, or oligomer. The term "polypeptide" is also intended to include fragments, analogues and derivatives of a polypeptide wherein the fragment, analogue or derivative retains essentially the same biological activity or function as a reference protein.

According to a further aspect of the invention there is provided an antibody, or at least an effective binding part thereof, which binds an antigenic polypeptide, or part thereof, according to the invention.

As antibodies can be modified in a number of ways, the term "antibody" should be construed as covering any binding member or substance having a binding domain with the required specificity for the antigenic polypeptide. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

In a preferred aspect of the invention said antibody is a monoclonal antibody. Preferably said antibody is provided with a marker including a conventional label or tag, for example a radioactive and/or fluorescent and/or epitope label or tag. Antibodies, also known as immunoglobulins, are protein molecules which have specificity for foreign molecules (antigens) Immunoglobulins (Ig) are a class of structurally related proteins consisting of two pairs of polypeptide chains, one pair of light (L) (low molecular weight) chain (κ or λ), and one pair of heavy (H) chains (γ, α, μ, and ε), all four linked together by disulphide bonds. Both H and L chains have regions that contribute to the binding of antigen and that are highly variable from one Ig molecule to another. In addition, H and L chains contain regions that are non-variable or constant.

The L chains consist of two domains. The carboxy-terminal domain is essentially identical among L chains of a given type and is referred to as the "constant" (C) region. The amino terminal domain varies from L chain to L chain and contributes to the binding site of the antibody. Because of its variability, it is referred to as the "variable" (V) region.

The H chains of Ig molecules are of several classes, α, μ, σ, α, and γ (of which there are several sub-classes). An assembled Ig molecule consisting of one or more units of two identical H and L chains, derives its name from the H chain that it possesses. Thus, there are five Ig isotypes: IgA, IgM, IgD, IgE, and IgG (with four sub-classes based on the differences in the H chains, i.e., IgG1, IgG2, IgG3 and IgG4). Further detail regarding antibody structure and their various functions can be found in, Using Antibodies: A laboratory manual, Cold Spring Harbor Laboratory Press.

A preferred aspect of the invention provides a monoclonal antibody that is capable of specifically binding to the MCM2 polypeptide, or a variant polypeptide or fragment thereof, wherein the antibody is selected from the group consisting of:

(a) the monoclonal antibody produced by the hybridoma cell line as deposited with ECACC under deposit accession number 1310150. In compliance with 37 C.F.R. 1.809 we confirm that the deposit was made pursuant to these regulations. The viable hybridoma cell line (mycoplasma free) has the accession number 1310150 and was deposited on Oct. 15, 2013, with the Public Health England Porton Down and European Collection of Cell Cultures, Porton Down, Salisbury SP4 OJG, UK.

(b) a monoclonal antibody that binds to an epitope capable of binding the monoclonal antibody produced by the hybridoma cell line as deposited with ECACC under deposit accession number 13101501;

(c) a monoclonal antibody that binds to an isolated polypeptide according to the invention;

(d) a monoclonal antibody that is an antigen binding fragment of a monoclonal antibody of (a)-(d), wherein the fragment retains the capability of specifically binding to an MCM2 polypeptide, or a variant polypeptide or fragment thereof.

In a preferred embodiment, the monoclonal antibody binds to an epitope comprising the amino acid sequence represented in FIG. 1.

In an alternative embodiment, the monoclonal antibody binds to an epitope comprising the amino acid sequence represented in FIG. 2.

The invention further provides a method for producing a MCM2 antibody comprising immunizing an animal with an isolated polypeptide according to the invention.

In a preferred aspect, the invention provides a method for producing an MCM2 monoclonal antibody comprising:

(a) immunizing an immunocompetent animal with an antigenic polypeptide according to the invention under conditions to elicit an immune response;
(b) isolating antibody-producing cells from the animal;
(c) fusing the antibody-producing cells with immortalized cells in culture to form monoclonal antibody-producing hybridoma cells;
(d) culturing the hybridoma cells; and
(e) isolating monoclonal antibodies from culture.

The immunocompetent animal may be a mouse, rat or rabbit.

The invention also provides a hybridoma obtained by a method of the invention (step d).

The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

As used herein, "MCM2 antibody" refers to any antibody that specifically binds to MCM2 (FIG. 3), or to a variant or fragment thereof, and includes monoclonal antibodies, polyclonal antibodies, single-chain antibodies, and fragments thereof which retain the antigen binding function of the parent antibody.

The MCM2 antibodies of the invention are optimally monoclonal antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) Protein Eng. 8(10): 1057-1062); single-chain antibody molecules; and multispecific antibodies formed from antibody fragments.

In a yet further aspect of the invention there is provided a hybridoma cell line which produces a monoclonal antibody as hereinbefore described.

The present invention also provides a hybridoma as deposited with ECACC under deposit accession number 13101501.

In a further aspect, the invention provides a kit for diagnosing cancer comprising at least one monoclonal antibody according to the invention. Preferably the monoclonal antibody is the monoclonal antibody produced by the hybridoma cell line as deposited with ECACC under deposit accession number 13101501. The kit may further comprise an antibody that specifically binds to an MCM polypeptide, for example MCM 2 to 7, including MCM2, MCM3, MCM4, MCM5, MCM6 or an MCM7 polypeptide. The kit may comprise a combination of two or more different antibodies that specifically bind to an MCM polypeptide, for example, two different MCMs selected from the group consisting of MCM 3, 4, 5, 6, and 7. For example the MCM may include MCM2 and one other MCM selected from MCM 3, 4, 5, 6, and 7. In a preferred method of the invention, the MCM is selected from the group consisting of MCM 2, 5, and 7. In a further preferred method of the invention, the MCM is selected from the group consisting of MCM 2 and 7. Each antibody may be provided as a separate antibody reagent or all of the antibodies may be provided as an antibody cocktail.

The kit of the invention may further comprise a peroxidase blocking reagent, a protein blocking reagent, chemicals for the detection of antibody binding to said biomarker proteins, a counterstain, a bluing agent, and instructions for use.

The kit of the invention may further comprise reagents for Pap staining for example EA50 and Orange G.

The invention also provides a method for diagnosing cancer in a patient, the method comprising:

a) obtaining a body fluid or body tissue sample from the patient;

b) contacting the sample with a monoclonal antibody according to the invention that specifically binds to MCM2; and, c) detecting binding of the antibody to MCM2.

In a preferred embodiment, the monoclonal antibody is the monoclonal antibody produced by the hybridoma cell line as deposited with ECACC under deposit accession number 13101501.

The present invention also provides a conjugate comprising an antibody of the present invention and a detectable label. The detectable label may be any suitable label known in the art. For example, the label may be a radiolabel, a fluorescent label, an enzymatic label or contrast media.

It will be appreciated by those skilled in the art that the antibodies of the present invention may also be used to detect, quantitate and/or localize cells expressing MCM2.

A variety of immunoassays may be used in the methods of diagnosis. Such immunoassays include competitive and non-competitive assay systems using techniques such as immunocytochemistry, immunohistochemistry, radioimmunoassays, ELISA, "sandwich" immunoassays, precipitin reactions, gel diffusion precipitin reactions, immunodiffusion assays, agglutination assays, complement fixation assays, immunoradiometric assays, fluorescent immunoassays and the like. Both in vitro and in vivo assays can be used.

The sample obtained from the patient may comprise any bodily fluid, such as peripheral blood, plasma, lymphatic fluid, peritoneal fluid, cerebrospinal fluid, or pleural fluid, or any body tissue. In vitro binding may be performed using histological specimens or subfractions of tissue or fluid. In vivo binding may be achieved by administering the conjugate by any means known in the art (such as intravenous, intraperitoneal, intra-arterial, etc.) such that immunospecific binding may be detected.

In addition, imaging techniques may be used, in which an antibody of the present invention is bound to a suitable imaging label. The labelled antibody may be administered in vivo to determine the localization of MCM2 in a patient. Accordingly, the present invention also provides a method for diagnosing cancer in a subject, the method comprising administering to the patient an antibody of the present invention labeled with an imaging agent under conditions so as to form a complex between the antibody and cells presenting MCM2 in the patient, and imaging the complex.

The cancer to be detected may be selected from bladder cancer, prostate cancer, cervical cancer, colorectal cancer, kidney cancer, lung cancer, breast cancer, anal cancer, oral cancer, endometrial cancer and throat cancer. Preferably, the cancer is bladder cancer and/or prostate cancer.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following materials, methods and figures:

FIG. 1: Epitope sequence (SEQ ID NO.: 1, residues 682 to 687 of MCM 2 amino acid sequence).

FIG. 2: Epitope sequence (SEQ ID NO.: 2, residues 680 to 688 of MCM 2 amino acid sequence).

FIG. 3: MCM 2 full length amino acid sequence (SEQ ID NO.: 3) showing the location of the epitope represented in FIG. 2.

FIG. 4: DNA sequence SEQ ID NO.: 4 of the insert used in the cloning of MCM2 cDNA into a pGEX6P-1 vector.

FIG. 5: Protein sequence SEQ ID NO.: 5 of an expressed fusion protein GST-MCM2.

FIG. 6 Recognition of hydroxylamine generated MCM2 peptides using SDS-PAGE (Coomassie Blue staining) and Western-blot (MCM2 antibody).

Figure 7A:
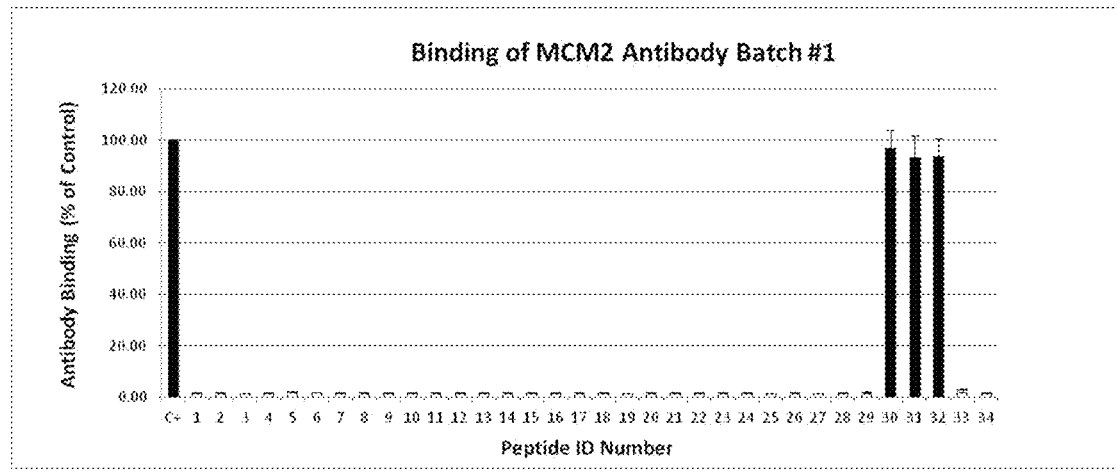
Figure 7B:
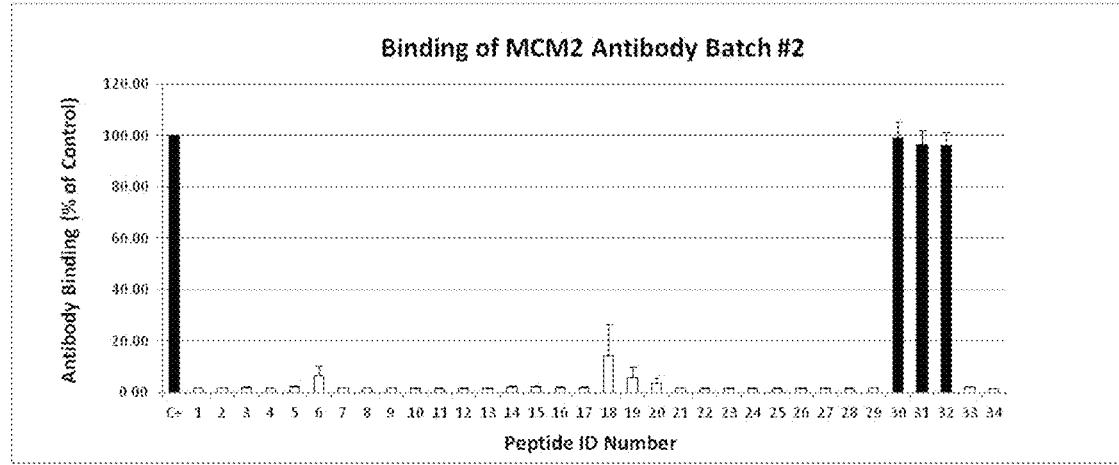

FIGS. 7A and 7B are charts showing the binding of MCM2 Antibody batches 1 and 2, respectively.

DETAILED DESCRIPTION OF THE INVENTION

Materials and Methods

Buffers for purification of GST-tagged proteins from *E. coli*:

Lysis Buffer: 50 mM Tris/HCl pH7.5, 250 mM NaCl, 1% Triton, 1 mM

EDTA, 1 mM EGTA, 0.1% β-Mercaptoethanol, 0.2 mM PMSF, 1 mM benzamidine

Equilibration Buffer: 50 mM Tris pH7.5

Wash Buffer: 250 mM NaCl, 0.03% Brij-35, 0.1 mM EGTA, 0.1% β-Mercaptoethanol, 0.2 mM PMSF, 1 mM benzamidine Elution: Wash buffer+20 mM glutathione (re-pH to 7.5)

Dialysis: 1) 50 mM Tris/HCl pH7.5, 0.1 mM EGTA, 150 mM NaCl, 50% glycerol, 0.03% Brij-35, 0.07% β-Mercaptoethanol, 1 mM Benzamidine, 0.1 mM PMSF; or 2) 50 mM Tris/HCl pH7.5, 0.1 mM EGTA, 150 mM NaCl, 270 mM sucrose, 0.03% Brij-35, 0.07% β Mercaptoethanol, 1 mM Benzamidine, 0.1 mM PMSF Buffers for Cyanogen bromide peptide cleavage:

Ammonium Bicarbonate 0.4M

2-Mercaptoethanol

Trifluoroacetic Acid-70% with water.

Buffers for Asparaginyl-glycyl peptide cleavage-Hydroxylamine:

Cleavage buffer: 2M Hydroxylamid HCL, 2MGuanidine HCL, 0.2M KCO3 pH 9.

Stopping sol: Trifluoracetic acid 2% (v/v water).

Buffers for Electro transfer and immunodetection:

Transfer buffer: 3 g Tris base, 14.4 g Glycine and 200 ml methanol, up to 1 L final volume.

Cloning and GST-MCM2 Protein Expression:

MCM2 cDNA was cloned into a pGEX-6P-1 vector (Addgene). The plasmid created was then transfected in *E. coli*. The transfected bacteria were then selected from not transfected using an ampicillin medium before being cultivated to synthesise the cloned MCM2.

TABLE 1

MCM2 cloning Information

| | |
|---|---|
| Plasmid Name | pGEX6P-1-Mcm2 |
| Expressed Protein | GST-Mcm2 |
| Parental Plasmid | pGEX-6P-1 |
| Restriction Sites Used | BamH1 EcoR1 |
| Antibiotic Selection | Amp |
| DNA Sequence of Insert | See FIG. 4 |
| Protein Sequence of Expressed Fusion Protein | See FIG. 5 |

Purification of GST-Tagged Proteins:

The transfected bacteria were harvested after an overnight culture by centrifugation at 5000 rpm for 30 mins. Bacteria were either lysed immediately for protein purification or frozen at −80° C. for further analysis. Either way, Lysis buffer was then added to the cells:

Large scale=20 ml of lysis buffer per 1 L of harvested culture.

Pilot scale=Use 35 ml of lysis buffer per 500 ml of harvested culture.

After 15 sec bursts of sonication on ice, the cell homogenate was then centrifuged at 15,000 rpm for 30 min to clarify lysate. The GSH-Sepharose (Pharmacia) was then washed several times using Equilibration buffer by spinning down resin at 2000 rpm for 2 min, removing the supernatant each time. The clarified lysate was then added to the GSH-Sepharose resin and incubated on roller at 4° C. for 45 mins. Following the incubation, the GSH-Sepharose resin was centrifuged at 2000 rpm for 2 min, the supernatant was removed and kept for further analysis.

The GSH-beads were then washed using Wash buffer. These washing steps were done by:

(A) Batch washing when there was a large volume of beads.

(B) Washing on a column when there was a small volume of beads.

The GSH beads were washed until the absorbance at 595 nm ($A_{595\ nm}$) is at or near zero.

The GST-Tagged Proteins were then Eluted by:

a) Batch elution. To batch elute, the same volume of Elution Buffer was added to beads i.e. 5 ml of elution buffer was added to 5 ml of beads. The buffer was incubated for 10 min on ice and then centrifuged at 2000 rpm for 2 min. The supernatant was then recovered. The elution was repeated a second time using half the volume of buffer to resin. The eluates were then combined and poured through a large yellow 100 ml Biorad column to remove any remaining resin. The protein concentration was measured on the flow through.

b) Eluting from column. Gently apply Elution buffer to the column without disturbing the resin. Measure the protein concentration of eluted fractions.

The eluted material was dialysed at 4° C. for 6-16 hours in either Dialysis buffer 1 or 2. The proteins were then stored at −20° C. or snapped freezed and stored at −80° C. depending on the specifications outlined in the SOP for the particular protein.

Cleavage of GST-MCM2 and Analysis of the Cleaved Proteins:

Asparaginyl-glycyl peptide cleavage-Hydroxylamine:

One volume of GST-protein solution (3 mg/ml protein) was added to 10 volumes of cleavage buffer. The sample was capped and incubated at 45° C. for 4 hr. The reaction was then stopped by the addition of 3 volumes of stopping solution. The sample was then concentrated using a vacuum concentrator, to a final volume of 200 μL before being stored at −20° C.

Analysis of Cleaved Proteins by SDS-PAGE:

Peptides generated from the cleavage were separated by SDS-PAGE using the NuPAGE system (Invitrogen) and Novex Bis Tris Mini Gels (12%) with MOPS running buffer. The samples were prepared by adding 4×LDS sample buffer (final conc 1×, Invitrogen) and DTT (100 mM). The samples were then heat denatured for 5 min at 95° C. before being loaded onto a gel.

The samples were run in duplication, one set was stained with coomassie blue, the other set was transferred overnight onto nitrocellulose membrane, for immuno-blot analysis with MCM2 antibody.

Coomassie Blue Staining:

The staining was performed using "SimplyBlue SafeStain" (Invitrogen) following manufacturer's instructions.

Once stained, gels were dried using "DryEase Mini-Gel Drying System" (Invitrogen) following manufacturer's instructions.

Electro Transfer and Immunodetection:

Proteins are transferred overnight at 11V on a nitrocellulose membrane (pore 0.2 micron) using the Bio-Rad mini Protean system. The membrane was then blocked in 5% nonfat milk/PBS tween 20 (0.1%) for 30 min, before adding the MCM2 antibody.

The diluted primary antibody (MCM2 at dilution 1/1000; or 1/2000 in the blocking solution) was incubated for 1 hr at room temperature. After incubation, the membrane was washed in blocking solution for 20 min, before adding the secondary antibody conjugate (1/10000 in blocking solution) for 1 hr at room temperature. The membrane was then washed twice with PBS/tween 20 (0.1%) for 20 min and then twice for 20 min in PBS. The detection was achieved by using "Hyper-film ECL" (Amersham).

ELISA Assay for Epitope Mapping:

1—Peptides were synthesized covering the entire length of this region.

2—ELISA assay—each synthetic biotinylated peptide is plated per well of a 96-wells plate coated with streptavidin.

3—After washing, each single peptide per well is incubated with the novel mouse monoclonal MCM2 antibody (three different dilution of antibody are used: 0.1 μg/l, 1 μg/l and 10 μg/l).

4—After washing, each peptide is incubated with anti-mouse IgG secondary antibody conjugated to horseradish peroxidase.

5—After washing, the peptides specifically bound by the MCM2 antibody are revealed and quantified by spectrophometry after incubation with tetramethylbenzidine (TMB). Only wells containing the peptides specifically recognized by the novel MCM2 antibody of the present invention become blue and are identified as a epitope comprising peptide. The intensity of this blue colored product (450 nm) is directly proportional to the concentration of bound antibodies.

Dissolving Peptides:

Followed manufacturer (Mimotopes) protocol.

In 80% DMSO.

Dilution Peptides before use:

Followed manufacturer (Mimotopes) protocol.

Dilution 1/1000 in PBS Tween20 azide solution.

Elisa:

Add 100 μl of diluted peptide in well (using Streptavidin-coated plates, Thermo

Scientific #15500).
Leave at RT for 2 h, flick out solution.
Wash 2 times with 200 µl PBS/Tween20 (flick out solution).
Block with 200 µl (5% milk in PBS Tween20) for 2 h at RT.
Dilute MCM2 Antibody (kind gift from the University of Cambridge) in 5% milk PBS Tween20,
Add 100 µl by well of MCM2 Antibody by well,
Leave 1 h at RT.
Wash 2 times with 200 µl PBS Tween20 (flick out solution).
Dilute 2$^{nd}$ Antibody anti-mouse (Jackson goat anti-mouse),
Add 100 µl by well of 2$^{nd}$ antibody,
Leave 1 h at RT.
Wash 3 times with 200 µl PBS Tween20 (flick out solution).
Add 100 µl by well of TMB (TMB Substrate Kit, Thermo Scientific #34021).
Leave 20 min at RT in dark.
Add 100 µl of Stop solution (2M Sulfuric Acid).
Read the plate at 450 nm absorbance.

Identification of Key Amino Acids Constituting the Epitope of the MCM2 Monoclonal Antibody:

Following the identification of the epitope using the SDS-PAGE and ELISA methods above, synthesis of peptides covering the entire length of the epitope peptide were obtained where for each peptide a different amino-acid residue in the epitope peptide is substituted with alanine. Such synthesized peptides were plated one biotinylated synthetic peptide per well of a 96-wells streptavidin coated plate. Following which an ELISA assay was performed as described above using the novel MCM2 antibody. Alanine-modified peptides not-recognized by the novel MCM2 antibody did not become blue, whereas those recognized by the novel MCM2 antibody turned blue. Accordingly, the key amino-acids constituting the epitope of this novel antibody were identified.

Hydroxylamine cleavage of GST-MCM2 recombinant protein: Hydroxylamine cleavage should generate the following set of peptides:

Peptide 1 (17 kDa)
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLN

Peptide 2: p2 (58.5 kDa)
GDHVTHPDFMLYDALDVVLYMDPMCLDAFPKLVCFKKRIEAIPQIDKYLK

SSKYIAWPLQGWQATFGGGDHPPKLEVLFQGPLGSPQFPGRLERPHMASS

PAQRRRGNDPLTSSPGRSSRRTDALTSSPGRDLPPFEDESEGLLGTEGPL

EEEEDGEELIGDGMERDYRAIPELDAYEAEGLALDDEDVEELTASQREAA

ERAMRQRDREAGRGLGRMRRGLLYDSDEEDEERPARKRRQVERATEDGEE

DEEMIESIENLEDLKGHSVREWVSMAGPRLEIHHRFKNFLRTHVDSHGHN

VFKERISDMCKENRESLVVNYEDLAAREHVLAYFLPEAPAELLQIFDEAA

LEVVLAMYPKYDRITNHIHVRISHLPLVEELRSLRQLHLNQLIRTSGVVT

SCTGVLPQLSMVKYNCNKCNFVLGPFCQSQNQEVKPGSCPECQSAGPFEV

NMEETIYQNYQRIRIQESPGKVAAGRLPRSKDAILLADLVDSCKPGDEIE

LTGIYHNNYDGSLNTAN

Peptide 3 p3 (29.024 kDa)
GFPVFATVILANHVAKKDNKVAVGELTDEDVKMITSLSKDQQIGEKIFAS

IAPSIYGHEDIKRGLALALFGGEPKNPGGKHKVRGDINVLLCGDPGTAKS

QFLKYIEKVSSRAIFTTGQGASAVGLTAYVQRHPVSREWTLEAGALVLAD

RGVCLIDEFDKMNDQDRTSIHEAMEQQSISISKAGIVTSLQARCTVIAAA

NPIGGRYDPSLTFSENVDLTEPIISRFDILCVVRDTVDPVQDEMLARFVV

GSHVRHHPSNKEEEGLAN

Peptide 4: p4 (24.3 kDa)
GSAAEPAMPNTYGVEPLPQEVLKKYIIYAKERVHPKLNQMDQDKVAKMYS

DLRKESMATGSIPITVRHIESMIRMAEAHARIHLRDYVIEDDVNMAIRVM

LESFIDTQKFSVMRSMRKTFARYLSFRRDNNELLLFILKQLVAEQVTYQR

NRFGAQQDTIEVPEKDLVDKARQINIHNLSAFYDSELFRMNKFSHDLKRK

MILQQF

But there was also Incomplete Digestion:
Not digested GST-MCM2: 130 kD
P1+p2+p3: 104.6 kD
P2+p3+p4: 112 kD
P1+p2=75.6 kD
P2+p3=87.6 kD
P3+p4=53.3 kD Results
Stage 1: Location of Epitope within the Peptides Population Peptides with MW ~30 kDa, ~55 kDa, ~90 kDa and >100 kDa were recognised by the MCM2 antibody. This is consistent with a location of the epitope within the peptide #3.

Stage 2: Identification of Epitope within the Peptide #3
A first experiment with peptides covering the first half of the peptide #3 didn't give any results, highlighting the fact that the location of the epitope was on the second half of the peptide #3.

A second experiment has been carried out with a new set of 34 peptides.

The 2 batches of MCM2 antibodies (Batch 1 GBC antibody and Batch 2 AbD Serotec antibody) bound to the same peptides (peptides number 30, 31, 32) demonstrating that these antibodies are identical. See, FIGS. 7A and 7B. The amino acid sequences of the peptides recognized by both antibodies are:

Sequences of Peptides 29 to 34
29    Biotin- SGSGQDEMLARFVVGSHVR -NH2

30    Biotin- SGSGMLARFVVGSHVRHHP -NH2

31    Biotin- SGSGRFVVGSHVRHHPSNK -NH2

32    Biotin- SGSGVGSHVRHHPSNKEEE -NH2

33    Biotin- SGSGHVRHHPSNKEEEGLA -NH2

34    Biotin- SGSGVRHHPSNKEEEGLAN -NH2
So it recognizes with strong affinity epitope:
VGSHVRHHP.

The amino acid sequence common to these 3 peptides is VGSHVRHHP, and therefore correspond to the epitope recognized by both antibodies.

Stage 3: Alanine Scanning Analysis of the MCM2 Antibody Epitope
A new set of peptides has been generated in which each amino acid has been replaced by an Alanine.

| Peptides | VGSHVRHHP | | |
|---|---|---|---|
| 1 | 0.25 | 1,538.72 | Biotin- SGSGVGSHVRHHP -NH2 |
| 2 | 0.19 | 1,510.67 | Biotin- SGSGAGSHVRHHP -NH2 |
| 3 | 0.28 | 1,552.75 | Biotin- SGSGVASHVRHHP -NH2 |
| 4 | 0.28 | 1,522.72 | Biotin- SGSGVGAHVRHHP -NH2 |
| 5 | 0.27 | 1,472.66 | Biotin- SGSGVGSAVRHHP -NH2 |
| 6 | 0.19 | 1,510.67 | Biotin- SGSGVGSHARHHP -NH2 |
| 7 | 0.34 | 1,453.61 | Biotin- SGSGVGSHVAHHP -NH2 |
| 8 | 0.27 | 1,472.66 | Biotin- SGSGVGSHVRAHP -NH2 |
| 9 | 0.27 | 1,472.66 | Biotin- SGSGVGSHVRHAP -NH2 |
| 10 | 0.23 | 1,512.68 | Biotin- SGSGVGSHVRHHA -NH2 |
| 11 | 0.21 | 1,566.73 | Biotin- SGSGVGDHVRHHP -NH2 |

Results—

| | peptide ID | | | | | | | | | | | |
|---|---|---|---|---|---|---|---|---|---|---|---|---|
| | 1 | 2 | 3 | 4 | 5 | 6 | 7 | 8 | 9 | 10 | 11 | C+ |
| Batch 1 | 2.7966 | 2.864 | 2.8164 | 2.7755 | 2.7361 | 2.7584 | 2.4617 | 0.0751 | 2.3274 | 2.6784 | 1.6169 | 3.2615 |

| | peptide ID | | | | | | | | | | | |
|---|---|---|---|---|---|---|---|---|---|---|---|---|
| 1/5000 | 1 | 2 | 3 | 4 | 5 | 6 | 7 | 8 | 9 | 10 | 11 | C− |
| Batch 2 | 3.4266 | 303523 | 303217 | 3.1951 | 302383 | 3.1454 | 3.1893 | 0.0662 | 2.8478 | 3.2171 | 3.3807 | 0.0852 |

The antibody (both purification) recognizes very well peptide 1, 2, 3 and 10 but has a reduced binding for peptides 4, 5, 6, 7. Therefore, the epitope VGSHVRHHP identified previously can be narrowed down to ShvRHH.

The antibody has no binding for peptide 8 and weak for 9.

In peptide 4, the serine (SER682) was changed into alanine and binding was lost demonstrating that the serine is part of the epitope.

Summary of MCM-2 Feasibility and Verifications Studies

Feasibility and verification studies were conducted at three UK sites, on a combined population of 247 patients attending either Cystoscopic Surveillance Clinic ("CS") for monitoring for recurrence of bladder cancer flowing treatment, or Gross Haematuria Clinics ("GH") for initial diagnosis of bladder cancer plus 50 healthy controls.

Briefly, cells were captured from patient urine by centrifugation, the cells were fixed on cytology slides, and then stained using the anti-MCM-2 antibody of the present invention. The total number of cells plus number of MCM-2 positive cells were counted by aid of a microscope. If the number of MCM2 positive cells fell below 50 in the GH population or below 200 in the CS population, the patient was shown to have no bladder cancer, if they fell above these thresholds the patient was shown to have bladder cancer. Confirmation of the bladder cancer result was assessed by the gold standard diagnostic procedure, cystoscopy and biopsy.

This study demonstrated the viability of using the anti-MCM-2 antibody described in this patent application as a diagnostic determinant of bladder cancer.

| | Cytosystems Ltd[1] | | Cystoscopy[2] | Cytology[2] |
|---|---|---|---|---|
| | GH | CS | | |
| Sensitivity | 97% | 89% | 92% | 35% |
| Specificity | 90% | 92% | 88% | 79% |

2 = Schiake et al. 2012Can J Uroi 19(4):6345-50

What is claimed is:

1. A hybridoma cell line as deposited with ECACC under deposit accession number 13101501.

2. A kit for diagnosing cancer comprising at least one monoclonal antibody, wherein the monoclonal antibody is the monoclonal antibody produced by the hybridoma cell line as deposited with ECACC under deposit accession number 13101501.

3. The kit as claimed in claim 2 further comprising an additional antibody that specifically binds to an MCM3, MCM4, MCM5, MCM6 or an MCM7 polypeptide.

4. The kit as claimed in claim 3 wherein the additional antibody specifically binds to an MCM2, MCM5, or MCM7 polypeptide.

5. The kit as claimed in claim 4 wherein the additional antibody specifically binds to the MCM7 polypeptide.

6. The kit as claimed in claim 2 wherein the kit further comprises a peroxidase blocking reagent, a protein blocking reagent, chemicals for the detection of antibody binding to said biomarker proteins, a counterstain, a bluing agent, and instructions for use.

7. An antibody produced from the hybridoma cell line of claim 1, as deposited with ECACC under deposit accession number 13101501.

* * * * *

SEQUENCE LISTING

<160> NUMBER OF SEQ ID NOS: 26

<210> SEQ ID NO 1
<211> LENGTH: 144
<212> TYPE: PRT
<213> ORGANISM: Homo sapiens

<400> SEQUENCE: 1

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

<210> SEQ ID NO 2
<211> LENGTH: 517
<212> TYPE: PRT
<213> ORGANISM: Homo sapiens

<400> SEQUENCE: 2

Gly Asp His Val Thr His Pro Asp Phe Met Leu Tyr Asp Ala Leu Asp
1               5                   10                  15

Val Val Leu Tyr Met Asp Pro Met Cys Leu Asp Ala Phe Pro Lys Leu
            20                  25                  30

Val Cys Phe Lys Lys Arg Ile Glu Ala Ile Pro Gln Ile Asp Lys Tyr
        35                  40                  45

Leu Lys Ser Ser Lys Tyr Ile Ala Trp Pro Leu Gln Gly Trp Gln Ala
50                  55                  60

Thr Phe Gly Gly Gly Asp His Pro Pro Lys Leu Glu Val Leu Phe Gln
65                  70                  75                  80

Gly Pro Leu Gly Ser Pro Gln Phe Pro Gly Arg Leu Glu Arg Pro His
                85                  90                  95

Met Ala Ser Ser Pro Ala Gln Arg Arg Arg Gly Asn Asp Pro Leu Thr
            100                 105                 110

Ser Ser Pro Gly Arg Ser Ser Arg Arg Thr Asp Ala Leu Thr Ser Ser
        115                 120                 125

Pro Gly Arg Asp Leu Pro Pro Phe Glu Asp Glu Ser Glu Gly Leu Leu
130                 135                 140

Gly Thr Glu Gly Pro Leu Glu Glu Glu Glu Asp Gly Glu Glu Leu Ile
145                 150                 155                 160

Gly Asp Gly Met Glu Arg Asp Tyr Arg Ala Ile Pro Glu Leu Asp Ala
                165                 170                 175

Tyr Glu Ala Glu Gly Leu Ala Leu Asp Asp Glu Asp Val Glu Glu Leu

```
                    180                 185                 190
        Thr Ala Ser Gln Arg Glu Ala Ala Glu Arg Ala Met Arg Gln Arg Asp
                        195                 200                 205
        Arg Glu Ala Gly Arg Gly Leu Gly Arg Met Arg Arg Gly Leu Leu Tyr
                        210                 215                 220
        Asp Ser Asp Glu Glu Asp Glu Arg Pro Ala Arg Lys Arg Arg Gln
        225                 230                 235                 240
        Val Glu Arg Ala Thr Glu Asp Gly Glu Asp Glu Glu Met Ile Glu
                        245                 250                 255
        Ser Ile Glu Asn Leu Glu Asp Leu Lys Gly His Ser Val Arg Glu Trp
                        260                 265                 270
        Val Ser Met Ala Gly Pro Arg Leu Glu Ile His His Arg Phe Lys Asn
                        275                 280                 285
        Phe Leu Arg Thr His Val Asp Ser His Gly His Asn Val Phe Lys Glu
                        290                 295                 300
        Arg Ile Ser Asp Met Cys Lys Glu Asn Arg Glu Ser Leu Val Val Asn
        305                 310                 315                 320
        Tyr Glu Asp Leu Ala Ala Arg Glu His Val Leu Ala Tyr Phe Leu Pro
                        325                 330                 335
        Glu Ala Pro Ala Glu Leu Leu Gln Ile Phe Asp Glu Ala Ala Leu Glu
                        340                 345                 350
        Val Val Leu Ala Met Tyr Pro Lys Tyr Asp Arg Ile Thr Asn His Ile
                        355                 360                 365
        His Val Arg Ile Ser His Leu Pro Leu Val Glu Glu Leu Arg Ser Leu
                        370                 375                 380
        Arg Gln Leu His Leu Asn Gln Leu Ile Arg Thr Ser Gly Val Val Thr
        385                 390                 395                 400
        Ser Cys Thr Gly Val Leu Pro Gln Leu Ser Met Val Lys Tyr Asn Cys
                        405                 410                 415
        Asn Lys Cys Asn Phe Val Leu Gly Pro Phe Cys Gln Ser Gln Asn Gln
                        420                 425                 430
        Glu Val Lys Pro Gly Ser Cys Pro Glu Cys Gln Ser Ala Gly Pro Phe
                        435                 440                 445
        Glu Val Asn Met Glu Glu Thr Ile Tyr Gln Asn Tyr Gln Arg Ile Arg
                        450                 455                 460
        Ile Gln Glu Ser Pro Gly Lys Val Ala Ala Gly Arg Leu Pro Arg Ser
        465                 470                 475                 480
        Lys Asp Ala Ile Leu Leu Ala Asp Leu Val Asp Ser Cys Lys Pro Gly
                        485                 490                 495
        Asp Glu Ile Glu Leu Thr Gly Ile Tyr His Asn Asn Tyr Asp Gly Ser
                        500                 505                 510
        Leu Asn Thr Ala Asn
                515

<210> SEQ ID NO 3
<211> LENGTH: 268
<212> TYPE: PRT
<213> ORGANISM: Homo sapiens

<400> SEQUENCE: 3

Gly Phe Pro Val Phe Ala Thr Val Ile Leu Ala Asn His Val Ala Lys
1               5                   10                  15
Lys Asp Asn Lys Val Ala Val Gly Glu Leu Thr Asp Glu Asp Val Lys
                20                  25                  30
```

```
Met Ile Thr Ser Leu Ser Lys Asp Gln Gln Ile Gly Glu Lys Ile Phe
            35                  40                  45

Ala Ser Ile Ala Pro Ser Ile Tyr Gly His Glu Asp Ile Lys Arg Gly
 50                  55                  60

Leu Ala Leu Ala Leu Phe Gly Gly Glu Pro Lys Asn Pro Gly Gly Lys
 65                  70                  75                  80

His Lys Val Arg Gly Asp Ile Asn Val Leu Leu Cys Gly Asp Pro Gly
             85                  90                  95

Thr Ala Lys Ser Gln Phe Leu Lys Tyr Ile Glu Lys Val Ser Ser Arg
            100                 105                 110

Ala Ile Phe Thr Thr Gly Gln Gly Ala Ser Ala Val Gly Leu Thr Ala
            115                 120                 125

Tyr Val Gln Arg His Pro Val Ser Arg Glu Trp Thr Leu Glu Ala Gly
            130                 135                 140

Ala Leu Val Leu Ala Asp Arg Gly Val Cys Leu Ile Asp Glu Phe Asp
145                 150                 155                 160

Lys Met Asn Asp Gln Asp Arg Thr Ser Ile His Glu Ala Met Glu Gln
            165                 170                 175

Gln Ser Ile Ser Ile Ser Lys Ala Gly Ile Val Thr Ser Leu Gln Ala
            180                 185                 190

Arg Cys Thr Val Ile Ala Ala Asn Pro Ile Gly Gly Arg Tyr Asp
            195                 200                 205

Pro Ser Leu Thr Phe Ser Glu Asn Val Asp Leu Thr Glu Pro Ile Ile
            210                 215                 220

Ser Arg Phe Asp Ile Leu Cys Val Val Arg Asp Thr Val Asp Pro Val
225                 230                 235                 240

Gln Asp Glu Met Leu Ala Arg Phe Val Val Gly Ser His Val Arg His
            245                 250                 255

His Pro Ser Asn Lys Glu Glu Glu Gly Leu Ala Asn
            260                 265

<210> SEQ ID NO 4
<211> LENGTH: 206
<212> TYPE: PRT
<213> ORGANISM: Homo sapiens

<400> SEQUENCE: 4

Gly Ser Ala Ala Glu Pro Ala Met Pro Asn Thr Tyr Gly Val Glu Pro
 1               5                  10                  15

Leu Pro Gln Glu Val Leu Lys Lys Tyr Ile Ile Tyr Ala Lys Glu Arg
            20                  25                  30

Val His Pro Lys Leu Asn Gln Met Asp Gln Asp Lys Val Ala Lys Met
            35                  40                  45

Tyr Ser Asp Leu Arg Lys Ser Met Ala Thr Gly Ser Ile Pro Ile
 50                  55                  60

Thr Val Arg His Ile Glu Ser Met Ile Arg Met Ala Glu Ala His Ala
 65                  70                  75                  80

Arg Ile His Leu Arg Asp Tyr Val Ile Glu Asp Val Asn Met Ala
            85                  90                  95

Ile Arg Val Met Leu Glu Ser Phe Ile Asp Thr Gln Lys Phe Ser Val
            100                 105                 110

Met Arg Ser Met Arg Lys Thr Phe Ala Arg Tyr Leu Ser Phe Arg Arg
            115                 120                 125

Asp Asn Asn Glu Leu Leu Leu Phe Ile Leu Lys Gln Leu Val Ala Glu
            130                 135                 140
```

Gln Val Thr Tyr Gln Arg Asn Arg Phe Gly Ala Gln Gln Asp Thr Ile
145                 150                 155                 160

Glu Val Pro Glu Lys Asp Leu Val Asp Lys Ala Arg Gln Ile Asn Ile
                165                 170                 175

His Asn Leu Ser Ala Phe Tyr Asp Ser Glu Leu Phe Arg Met Asn Lys
            180                 185                 190

Phe Ser His Asp Leu Lys Arg Lys Met Ile Leu Gln Gln Phe
            195                 200                 205

<210> SEQ ID NO 5
<211> LENGTH: 19
<212> TYPE: PRT
<213> ORGANISM: Homo sapiens

<400> SEQUENCE: 5

Ser Gly Ser Gly Gln Asp Glu Met Leu Ala Arg Phe Val Val Gly Ser
1               5                   10                  15

His Val Arg

<210> SEQ ID NO 6
<211> LENGTH: 19
<212> TYPE: PRT
<213> ORGANISM: Homo sapiens

<400> SEQUENCE: 6

Ser Gly Ser Gly Met Leu Ala Arg Phe Val Val Gly Ser His Val Arg
1               5                   10                  15

His His Pro

<210> SEQ ID NO 7
<211> LENGTH: 19
<212> TYPE: PRT
<213> ORGANISM: Homo sapiens

<400> SEQUENCE: 7

Ser Gly Ser Gly Arg Phe Val Val Gly Ser His Val Arg His His Pro
1               5                   10                  15

Ser Asn Lys

<210> SEQ ID NO 8
<211> LENGTH: 19
<212> TYPE: PRT
<213> ORGANISM: Homo sapiens

<400> SEQUENCE: 8

Ser Gly Ser Gly Val Gly Ser His Val Arg His His Pro Ser Asn Lys
1               5                   10                  15

Glu Glu Glu

<210> SEQ ID NO 9
<211> LENGTH: 19
<212> TYPE: PRT
<213> ORGANISM: Homo sapiens

<400> SEQUENCE: 9

Ser Gly Ser Gly His Val Arg His His Pro Ser Asn Lys Glu Glu Glu
1               5                   10                  15

Gly Leu Ala

```
<210> SEQ ID NO 10
<211> LENGTH: 19
<212> TYPE: PRT
<213> ORGANISM: Homo sapiens

<400> SEQUENCE: 10

Ser Gly Ser Gly Val Arg His His Pro Ser Asn Lys Glu Glu Glu Gly
1               5                   10                  15

Leu Ala Asn

<210> SEQ ID NO 11
<211> LENGTH: 9
<212> TYPE: PRT
<213> ORGANISM: Homo sapiens

<400> SEQUENCE: 11

Val Gly Ser His Val Arg His His Pro
1               5

<210> SEQ ID NO 12
<211> LENGTH: 13
<212> TYPE: PRT
<213> ORGANISM: Homo sapiens

<400> SEQUENCE: 12

Ser Gly Ser Gly Val Gly Ser His Val Arg His His Pro
1               5                   10

<210> SEQ ID NO 13
<211> LENGTH: 13
<212> TYPE: PRT
<213> ORGANISM: Homo sapiens

<400> SEQUENCE: 13

Ser Gly Ser Gly Ala Gly Ser His Val Arg His His Pro
1               5                   10

<210> SEQ ID NO 14
<211> LENGTH: 13
<212> TYPE: PRT
<213> ORGANISM: Homo sapiens

<400> SEQUENCE: 14

Ser Gly Ser Gly Val Ala Ser His Val Arg His His Pro
1               5                   10

<210> SEQ ID NO 15
<211> LENGTH: 13
<212> TYPE: PRT
<213> ORGANISM: Homo sapiens

<400> SEQUENCE: 15

Ser Gly Ser Gly Val Gly Ala His Val Arg His His Pro
1               5                   10

<210> SEQ ID NO 16
<211> LENGTH: 13
<212> TYPE: PRT
<213> ORGANISM: Homo sapiens

<400> SEQUENCE: 16

Ser Gly Ser Gly Val Gly Ser Ala Val Arg His His Pro
1               5                   10
```

```
<210> SEQ ID NO 17
<211> LENGTH: 13
<212> TYPE: PRT
<213> ORGANISM: Homo sapiens

<400> SEQUENCE: 17

Ser Gly Ser Gly Val Gly Ser His Ala Arg His His Pro
1               5                   10

<210> SEQ ID NO 18
<211> LENGTH: 13
<212> TYPE: PRT
<213> ORGANISM: Homo sapiens

<400> SEQUENCE: 18

Ser Gly Ser Gly Val Gly Ser His Val Ala His His Pro
1               5                   10

<210> SEQ ID NO 19
<211> LENGTH: 13
<212> TYPE: PRT
<213> ORGANISM: Homo sapiens

<400> SEQUENCE: 19

Ser Gly Ser Gly Val Gly Ser His Val Arg Ala His Pro
1               5                   10

<210> SEQ ID NO 20
<211> LENGTH: 13
<212> TYPE: PRT
<213> ORGANISM: Homo sapiens

<400> SEQUENCE: 20

Ser Gly Ser Gly Val Gly Ser His Val Arg His Ala Pro
1               5                   10

<210> SEQ ID NO 21
<211> LENGTH: 13
<212> TYPE: PRT
<213> ORGANISM: Homo sapiens

<400> SEQUENCE: 21

Ser Gly Ser Gly Val Gly Ser His Val Arg His His Ala
1               5                   10

<210> SEQ ID NO 22
<211> LENGTH: 13
<212> TYPE: PRT
<213> ORGANISM: Homo sapiens

<400> SEQUENCE: 22

Ser Gly Ser Gly Val Gly Asp His Val Arg His His Pro
1               5                   10

<210> SEQ ID NO 23
<211> LENGTH: 6
<212> TYPE: PRT
<213> ORGANISM: Homo sapiens

<400> SEQUENCE: 23

Ser His Val Arg His His
1               5

<210> SEQ ID NO 24
<211> LENGTH: 904
```

<212> TYPE: PRT
<213> ORGANISM: Homo sapiens

<400> SEQUENCE: 24

Met Ala Glu Ser Ser Glu Ser Phe Thr Met Ala Ser Ser Pro Ala Gln
1               5                   10                  15

Arg Arg Arg Gly Asn Asp Pro Leu Thr Ser Ser Pro Gly Arg Ser Ser
                20                  25                  30

Arg Arg Thr Asp Ala Leu Thr Ser Ser Pro Gly Arg Asp Leu Pro Pro
            35                  40                  45

Phe Glu Asp Glu Ser Glu Gly Leu Leu Gly Thr Glu Gly Pro Leu Glu
        50                  55                  60

Glu Glu Glu Asp Gly Glu Glu Leu Ile Gly Asp Gly Met Glu Arg Asp
65                  70                  75                  80

Tyr Arg Ala Ile Pro Glu Leu Asp Ala Tyr Glu Ala Glu Gly Leu Ala
                85                  90                  95

Leu Asp Asp Glu Asp Val Glu Glu Leu Thr Ala Ser Gln Arg Glu Ala
                100                 105                 110

Ala Glu Arg Ala Met Arg Gln Arg Asp Arg Glu Ala Gly Arg Gly Leu
            115                 120                 125

Gly Arg Met Arg Arg Gly Leu Leu Tyr Asp Ser Asp Glu Glu Asp Glu
        130                 135                 140

Glu Arg Pro Ala Arg Lys Arg Arg Gln Val Glu Arg Ala Thr Glu Asp
145                 150                 155                 160

Gly Glu Glu Asp Glu Glu Met Ile Glu Ser Ile Glu Asn Leu Glu Asp
                165                 170                 175

Leu Lys Gly His Ser Val Arg Glu Trp Val Ser Met Ala Gly Pro Arg
                180                 185                 190

Leu Glu Ile His His Arg Phe Lys Asn Phe Leu Arg Thr His Val Asp
            195                 200                 205

Ser His Gly His Asn Val Phe Lys Glu Arg Ile Ser Asp Met Cys Lys
        210                 215                 220

Glu Asn Arg Glu Ser Leu Val Val Asn Tyr Glu Asp Leu Ala Ala Arg
225                 230                 235                 240

Glu His Val Leu Ala Tyr Phe Leu Pro Glu Ala Pro Ala Glu Leu Leu
                245                 250                 255

Gln Ile Phe Asp Glu Ala Ala Leu Glu Val Val Leu Ala Met Tyr Pro
            260                 265                 270

Lys Tyr Asp Arg Ile Thr Asn His Ile His Val Arg Ile Ser His Leu
        275                 280                 285

Pro Leu Val Glu Glu Leu Arg Ser Leu Arg Gln Leu His Leu Asn Gln
290                 295                 300

Leu Ile Arg Thr Ser Gly Val Val Thr Ser Cys Thr Gly Val Leu Pro
305                 310                 315                 320

Gln Leu Ser Met Val Lys Tyr Asn Cys Asn Lys Cys Asn Phe Val Leu
                325                 330                 335

Gly Pro Phe Cys Gln Ser Gln Asn Gln Glu Val Lys Pro Gly Ser Cys
            340                 345                 350

Pro Glu Cys Gln Ser Ala Gly Pro Phe Glu Val Asn Met Glu Glu Thr
        355                 360                 365

Ile Tyr Gln Asn Tyr Gln Arg Ile Arg Ile Gln Glu Ser Pro Gly Lys
    370                 375                 380

Val Ala Ala Gly Arg Leu Pro Arg Ser Lys Asp Ala Ile Leu Leu Ala
385                 390                 395                 400

```
Asp Leu Val Asp Ser Cys Lys Pro Gly Asp Glu Ile Glu Leu Thr Gly
            405                 410                 415

Ile Tyr His Asn Asn Tyr Asp Gly Ser Leu Asn Thr Ala Asn Gly Phe
        420                 425                 430

Pro Val Phe Ala Thr Val Ile Leu Ala Asn His Val Ala Lys Lys Asp
            435                 440                 445

Asn Lys Val Ala Val Gly Glu Leu Thr Asp Glu Asp Val Lys Met Ile
        450                 455                 460

Thr Ser Leu Ser Lys Asp Gln Gln Ile Gly Glu Lys Ile Phe Ala Ser
465                 470                 475                 480

Ile Ala Pro Ser Ile Tyr Gly His Glu Asp Ile Lys Arg Gly Leu Ala
            485                 490                 495

Leu Ala Leu Phe Gly Gly Glu Pro Lys Asn Pro Gly Gly Lys His Lys
            500                 505                 510

Val Arg Gly Asp Ile Asn Val Leu Leu Cys Gly Asp Pro Gly Thr Ala
            515                 520                 525

Lys Ser Gln Phe Leu Lys Tyr Ile Glu Lys Val Ser Ser Arg Ala Ile
        530                 535                 540

Phe Thr Thr Gly Gln Gly Ala Ser Ala Val Gly Leu Thr Ala Tyr Val
545                 550                 555                 560

Gln Arg His Pro Val Ser Arg Glu Trp Thr Leu Glu Ala Gly Ala Leu
            565                 570                 575

Val Leu Ala Asp Arg Gly Val Cys Leu Ile Asp Glu Phe Asp Lys Met
            580                 585                 590

Asn Asp Gln Asp Arg Thr Ser Ile His Glu Ala Met Glu Gln Gln Ser
            595                 600                 605

Ile Ser Ile Ser Lys Ala Gly Ile Val Thr Ser Leu Gln Ala Arg Cys
        610                 615                 620

Thr Val Ile Ala Ala Asn Pro Ile Gly Gly Arg Tyr Asp Pro Ser
625                 630                 635                 640

Leu Thr Phe Ser Glu Asn Val Asp Leu Thr Glu Pro Ile Ile Ser Arg
            645                 650                 655

Phe Asp Ile Leu Cys Val Val Arg Asp Thr Val Asp Pro Val Gln Asp
            660                 665                 670

Glu Met Leu Ala Arg Phe Val Val Gly Ser His Val Arg His His Pro
        675                 680                 685

Ser Asn Lys Glu Glu Glu Gly Leu Ala Asn Gly Ser Ala Ala Glu Pro
        690                 695                 700

Ala Met Pro Asn Thr Tyr Gly Val Glu Pro Leu Pro Gln Glu Val Leu
705                 710                 715                 720

Lys Lys Tyr Ile Ile Tyr Ala Lys Glu Arg Val His Pro Lys Leu Asn
            725                 730                 735

Gln Met Asp Gln Asp Lys Val Ala Lys Met Tyr Ser Asp Leu Arg Lys
            740                 745                 750

Glu Ser Met Ala Thr Gly Ser Ile Pro Ile Thr Val Arg His Ile Glu
        755                 760                 765

Ser Met Ile Arg Met Ala Glu Ala His Ala Arg Ile His Leu Arg Asp
        770                 775                 780

Tyr Val Ile Glu Asp Asp Val Asn Met Ala Ile Arg Val Met Leu Glu
785                 790                 795                 800

Ser Phe Ile Asp Thr Gln Lys Phe Ser Val Met Arg Ser Met Arg Lys
            805                 810                 815
```

```
Thr Phe Ala Arg Tyr Leu Ser Phe Arg Arg Asp Asn Asn Glu Leu Leu
            820                 825                 830

Leu Phe Ile Leu Lys Gln Leu Val Ala Glu Gln Val Thr Tyr Gln Arg
        835                 840                 845

Asn Arg Phe Gly Ala Gln Gln Asp Thr Ile Glu Val Pro Glu Lys Asp
        850                 855                 860

Leu Val Asp Lys Ala Arg Gln Ile Asn Ile His Asn Leu Ser Ala Phe
865                 870                 875                 880

Tyr Asp Ser Glu Leu Phe Arg Met Asn Lys Phe Ser His Asp Leu Lys
                885                 890                 895

Arg Lys Met Ile Leu Gln Gln Phe
            900

<210> SEQ ID NO 25
<211> LENGTH: 2697
<212> TYPE: DNA
<213> ORGANISM: Homo sapiens

<400> SEQUENCE: 25
```

| | | | | | |
|---|---|---|---|---|---|
| ggatccgcat | ccagcccggc | ccagcgtcgg | cgaggcaatg | atcctctcac | ctccagccct | 60 |
| ggccgaagct | cccggcgtac | tgatgccctc | acctccagcc | ctggccgtga | ccttccacca | 120 |
| tttgaggatg | agtccgaggg | gctcctaggc | acagagggc | ccctggagga | agaagaggat | 180 |
| ggagaggagc | tcattggaga | tggcatggaa | agggactacc | gcgccatccc | agagctggac | 240 |
| gcctatgagg | ccgagggact | ggctctggat | gatgaggacg | tagaggagct | gacggccagt | 300 |
| cagagggagg | cagcagagcg | ggccatgcgg | cagcgtgacc | gggaggctgg | ccggggcctg | 360 |
| ggccgcatgc | gccgtgggct | cctgtatgac | agcgatgagg | aggacgagga | gcgccctgcc | 420 |
| cgcaagcgcc | gccaggtgga | gcgggccacg | gaggacggcg | aggaggacga | ggagatgatc | 480 |
| gagagcatcg | agaacctgga | ggatctcaaa | ggccactctg | tgcgcgagtg | ggtgagcatg | 540 |
| gcgggccccc | ggctggagat | ccaccaccgc | ttcaagaact | cctgcgcac | tcacgtcgac | 600 |
| agccacggcc | acaacgtctt | caaggagcgc | atcagcgaca | tgtgcaaaga | gaaccgtgag | 660 |
| agcctggtgg | tgaactatga | ggacttggca | gccaggagc | acgtgctggc | ctacttcctg | 720 |
| cctgaggcac | cggcggagct | gctgcagatc | tttgatgagg | ctgccctgga | ggtggtactg | 780 |
| gccatgtacc | ccaagtacga | ccgcatcacc | aaccacatcc | atgtccgcat | ctcccacctg | 840 |
| cctctggtgg | aggagctgcg | ctcgctgagg | cagctgcatc | tgaaccagct | gatccgcacc | 900 |
| agtggggtgg | tgaccagctg | cactggcgtc | ctgccccagc | tcagcatggt | caagtacaac | 960 |
| tgcaacaagt | gcaatttcgt | cctgggtcct | ttctgccagt | cccagaacca | ggaggtgaaa | 1020 |
| ccaggctcct | gtcctgagtg | ccagtcggcc | ggccccttg | aggtcaacat | ggaggagacc | 1080 |
| atctatcaga | actaccagcg | tatccgaatc | caggagagtc | aggcaaagt | ggcggctggc | 1140 |
| cggctgcccc | gctccaagga | cgccattctc | ctcgcagatc | tggtggacag | ctgcaagcca | 1200 |
| ggagacgaga | tagagctgac | tggcatctat | cacaacaact | atgatggctc | cctcaacact | 1260 |
| gccaatggct | tccctgtctt | tgccactgtc | atcctagcca | accacgtggc | caagaaggac | 1320 |
| aacaaggttg | ctgtagggga | actgaccgat | gaagatgtga | agatgatcac | tagcctctcc | 1380 |
| aaggatcagc | agatcggaga | gaagatcttt | gccagcattg | ctccttccat | ctatggtcat | 1440 |
| gaagacatca | agagaggcct | ggctctggcc | ctgttcggag | ggagcccaa | aaacccaggt | 1500 |
| ggcaagcaca | aggtacgtgg | tgatatcaac | gtgctcttgt | gcggagaccc | tggcacagcg | 1560 |
| aagtcgcagt | ttctcaagta | tattgagaaa | gtgtccagcc | gagccatctt | caccactggc | 1620 |

-continued

```
cagggggcgt cggctgtggg cctcacggcg tatgtccagc ggcaccctgt cagcagggag    1680
tggaccttgg aggctggggc cctggttctg gctgaccgag gagtgtgtct cattgatgaa    1740
tttgacaaga tgaatgacca ggacagaacc agcatccatg aggccatgga gcaacagagc    1800
atctccatct cgaaggctgg catcgtcacc tccctgcagg ctcgctgcac ggtcattgct    1860
gccgccaacc ccataggagg gcgctacgac ccctcgctga ctttctctga aacgtggac     1920
ctcacagagc ccatcatctc acgctttgac atcctgtgtg tggtgaggga caccgtggac    1980
ccagtccagg acgagatgct ggcccgcttc gtggtgggca gccacgtcag acaccacccc    2040
agcaacaagg aggaggaggg gctggccaat ggcagcgctg ctgagcccgc catgcccaac    2100
acgtatggcg tggagcccct gccccaggag gtcctgaaga agtacatcat ctacgccaag    2160
gagagggtcc acccgaagct caaccagatg gaccaggaca aggtggccaa gatgtacagt    2220
gacctgagga agaatctat ggcgacaggc agcatcccca ttacggtgcg gcacatcgag    2280
tccatgatcc gcatggcgga ggcccacgcg cgcatccatc tgcgggacta tgtgatcgaa    2340
gacgacgtca acatggccat ccgcgtgatg ctggagagct tcatagacac acagaagttc    2400
agcgtcatgc gcagcatgcg caagactttt gcccgctacc tttcattccg gcgtgacaac    2460
aatgagctgt tgctcttcat actgaagcag ttagtggcag agcaggtgac atatcagcgc    2520
aaccgctttg gggcccagca ggacactatt gaggtccctg agaaggactt ggtggataag    2580
gctcgtcaga tcaacatcca caacctctct gcattttatg acagtgagct cttcaggatg    2640
aacaagttca gccacgacct gaaaaggaaa atgatcctgc agcagttctg agaattc       2697
```

<210> SEQ ID NO 26
<211> LENGTH: 1125
<212> TYPE: PRT
<213> ORGANISM: Homo sapiens

<400> SEQUENCE: 26

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
```

-continued

```
                180                 185                 190
Leu Lys Ser Ser Lys Tyr Ile Ala Trp Pro Leu Gln Gly Trp Gln Ala
                195                 200                 205
Thr Phe Gly Gly Gly Asp His Pro Lys Ser Asp Leu Glu Val Leu
        210                 215                 220
Phe Gln Gly Pro Leu Gly Ser Ala Ser Ser Pro Ala Gln Arg Arg Arg
225                 230                 235                 240
Gly Asn Asp Pro Leu Thr Ser Ser Pro Gly Arg Ser Ser Arg Arg Thr
                245                 250                 255
Asp Ala Leu Thr Ser Ser Pro Gly Arg Asp Leu Pro Pro Phe Glu Asp
                260                 265                 270
Glu Ser Glu Gly Leu Leu Gly Thr Glu Gly Pro Leu Glu Glu Glu Glu
            275                 280                 285
Asp Gly Glu Glu Leu Ile Gly Asp Gly Met Glu Arg Asp Tyr Arg Ala
        290                 295                 300
Ile Pro Glu Leu Asp Ala Tyr Glu Ala Glu Gly Leu Ala Leu Asp Asp
305                 310                 315                 320
Glu Asp Val Glu Glu Leu Thr Ala Ser Gln Arg Glu Ala Ala Glu Arg
                325                 330                 335
Ala Met Arg Gln Arg Asp Arg Glu Ala Gly Arg Gly Leu Gly Arg Met
            340                 345                 350
Arg Arg Gly Leu Leu Tyr Asp Ser Asp Glu Glu Asp Glu Glu Arg Pro
        355                 360                 365
Ala Arg Lys Arg Arg Gln Val Glu Arg Ala Thr Glu Asp Gly Glu Glu
        370                 375                 380
Asp Glu Glu Met Ile Glu Ser Ile Glu Asn Leu Glu Asp Leu Lys Gly
385                 390                 395                 400
His Ser Val Arg Glu Trp Val Ser Met Ala Gly Pro Arg Leu Glu Ile
                405                 410                 415
His His Arg Phe Lys Asn Phe Leu Arg Thr His Val Asp Ser His Gly
            420                 425                 430
His Asn Val Phe Lys Glu Arg Ile Ser Asp Met Cys Lys Glu Asn Arg
        435                 440                 445
Glu Ser Leu Val Val Asn Tyr Glu Asp Leu Ala Ala Arg Glu His Val
    450                 455                 460
Leu Ala Tyr Phe Leu Pro Glu Ala Pro Ala Glu Leu Leu Gln Ile Phe
465                 470                 475                 480
Asp Glu Ala Ala Leu Glu Val Val Leu Ala Met Tyr Pro Lys Tyr Asp
                485                 490                 495
Arg Ile Thr Asn His Ile His Val Arg Ile Ser His Leu Pro Leu Val
                500                 505                 510
Glu Glu Leu Arg Ser Leu Arg Gln Leu His Leu Asn Gln Leu Ile Arg
            515                 520                 525
Thr Ser Gly Val Val Thr Ser Cys Thr Gly Val Leu Pro Gln Leu Ser
        530                 535                 540
Met Val Lys Tyr Asn Cys Asn Lys Cys Asn Phe Val Leu Gly Pro Phe
545                 550                 555                 560
Cys Gln Ser Gln Asn Gln Glu Val Lys Pro Gly Ser Cys Pro Glu Cys
                565                 570                 575
Gln Ser Ala Gly Pro Phe Glu Val Asn Met Glu Glu Thr Ile Tyr Gln
            580                 585                 590
Asn Tyr Gln Arg Ile Arg Ile Gln Glu Ser Pro Gly Lys Val Ala Ala
        595                 600                 605
```

```
Gly Arg Leu Pro Arg Ser Lys Asp Ala Ile Leu Leu Ala Asp Leu Val
        610                 615                 620

Asp Ser Cys Lys Pro Gly Asp Glu Ile Glu Leu Thr Gly Ile Tyr His
625                 630                 635                 640

Asn Asn Tyr Asp Gly Ser Leu Asn Thr Ala Asn Gly Phe Pro Val Phe
                645                 650                 655

Ala Thr Val Ile Leu Ala Asn His Val Ala Lys Lys Asp Asn Lys Val
            660                 665                 670

Ala Val Gly Glu Leu Thr Asp Glu Asp Val Lys Met Ile Thr Ser Leu
        675                 680                 685

Ser Lys Asp Gln Gln Ile Gly Glu Lys Ile Phe Ala Ser Ile Ala Pro
690                 695                 700

Ser Ile Tyr Gly His Glu Asp Ile Lys Arg Gly Leu Ala Leu Ala Leu
705                 710                 715                 720

Phe Gly Gly Glu Pro Lys Asn Pro Gly Gly Lys His Lys Val Arg Gly
                725                 730                 735

Asp Ile Asn Val Leu Leu Cys Gly Asp Pro Gly Thr Ala Lys Ser Gln
                740                 745                 750

Phe Leu Lys Tyr Ile Glu Lys Val Ser Ser Arg Ala Ile Phe Thr Thr
        755                 760                 765

Gly Gln Gly Ala Ser Ala Val Gly Leu Thr Ala Tyr Val Gln Arg His
770                 775                 780

Pro Val Ser Arg Glu Trp Thr Leu Glu Ala Gly Ala Leu Val Leu Ala
785                 790                 795                 800

Asp Arg Gly Val Cys Leu Ile Asp Glu Phe Asp Lys Met Asn Asp Gln
                805                 810                 815

Asp Arg Thr Ser Ile His Glu Ala Met Glu Gln Gln Ser Ile Ser Ile
                820                 825                 830

Ser Lys Ala Gly Ile Val Thr Ser Leu Gln Ala Arg Cys Thr Val Ile
            835                 840                 845

Ala Ala Ala Asn Pro Ile Gly Gly Arg Tyr Asp Pro Ser Leu Thr Phe
850                 855                 860

Ser Glu Asn Val Asp Leu Thr Glu Pro Ile Ile Ser Arg Phe Asp Ile
865                 870                 875                 880

Leu Cys Val Val Arg Asp Thr Val Asp Pro Val Gln Asp Glu Met Leu
                885                 890                 895

Ala Arg Phe Val Val Gly Ser His Val Arg His His Pro Ser Asn Lys
                900                 905                 910

Glu Glu Glu Gly Leu Ala Asn Gly Ser Ala Ala Glu Pro Ala Met Pro
            915                 920                 925

Asn Thr Tyr Gly Val Glu Pro Leu Pro Gln Glu Val Leu Lys Lys Tyr
930                 935                 940

Ile Ile Tyr Ala Lys Glu Arg Val His Pro Lys Leu Asn Gln Met Asp
945                 950                 955                 960

Gln Asp Lys Val Ala Lys Met Tyr Ser Asp Leu Arg Lys Glu Ser Met
                965                 970                 975

Ala Thr Gly Ser Ile Pro Ile Thr Val Arg His Ile Glu Ser Met Ile
            980                 985                 990

Arg Met Ala Glu Ala His Ala Arg Ile His Leu Arg Asp Tyr Val Ile
        995                 1000                1005

Glu Asp Asp Val Asn Met Ala Ile Arg Val Met Leu Glu Ser Phe
        1010                1015                1020
```

-continued

| | | | | | | | | | | | |
|---|---|---|---|---|---|---|---|---|---|---|---|
| Ile | Asp 1025 | Thr | Gln | Lys | Phe 1030 | Ser | Val | Met | Arg 1035 | Ser | Met | Arg | Lys | Thr |
| Phe | Ala 1040 | Arg | Tyr | Leu | Ser 1045 | Phe | Arg | Arg | Asp 1050 | Asn | Asn | Glu | Leu | Leu |
| Leu | Phe 1055 | Ile | Leu | Lys | Gln 1060 | Leu | Val | Ala | Glu 1065 | Gln | Val | Thr | Tyr | Gln |
| Arg | Asn 1070 | Arg | Phe | Gly | Ala 1075 | Gln | Gln | Asp | Thr 1080 | Ile | Glu | Val | Pro | Glu |
| Lys | Asp 1085 | Leu | Val | Asp | Lys 1090 | Ala | Arg | Gln | Ile 1095 | Asn | Ile | His | Asn | Leu |
| Ser | Ala 1100 | Phe | Tyr | Asp | Ser 1105 | Glu | Leu | Phe | Arg 1110 | Met | Asn | Lys | Phe | Ser |
| His | Asp 1115 | Leu | Lys | Arg | Lys 1120 | Met | Ile | Leu | Gln 1125 | Gln | Phe |